US011000394B2

(12) United States Patent
Pung et al.

(10) Patent No.: US 11,000,394 B2
(45) Date of Patent: May 11, 2021

(54) RELEASABLE DELIVERY SYSTEM

(71) Applicant: MicroVention, Inc., Aliso Viejo, CA (US)

(72) Inventors: Ponaka Pung, Signal Hill, CA (US); Tai D. Tieu, Fountain Valley, CA (US); Ross Soltanian, Glendale, CA (US); Helen Nguyen, Garden Grove, CA (US); Oanh Nguyen, Tustin, CA (US); Britney Ngo, Garden Grove, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 80 days.

(21) Appl. No.: 16/244,910

(22) Filed: Jan. 10, 2019

(65) Prior Publication Data

US 2019/0142617 A1 May 16, 2019

Related U.S. Application Data

(63) Continuation of application No. 15/269,782, filed on Sep. 19, 2016, now Pat. No. 10,182,931.

(Continued)

(51) Int. Cl.
*A61F 2/966* (2013.01)
*A61F 2/82* (2013.01)
*A61F 2/88* (2006.01)

(52) U.S. Cl.
CPC .............. *A61F 2/966* (2013.01); *A61F 2/82* (2013.01); *A61F 2/88* (2013.01);
(Continued)

(58) Field of Classification Search
CPC ...... A61F 2/82; A61F 2/88; A61F 2002/9665; A61F 2230/0069; A61F 2/966;
(Continued)

(56) References Cited

U.S. PATENT DOCUMENTS

| 5,824,041 A | 10/1998 | Lenker et al. |
| 6,623,518 B2 | 9/2003 | Thompson et al. |

(Continued)

FOREIGN PATENT DOCUMENTS

| JP | 2006-522668 A | 10/2006 |
| JP | 2014-533190 A | 12/2014 |

(Continued)

OTHER PUBLICATIONS

Japanese Patent Office, Office Action dated Aug. 11, 2020 with English translation in Japanese Patent Application No. 2018-514324, 7 pages.

(Continued)

*Primary Examiner* — Katrina M Stransky
(74) *Attorney, Agent, or Firm* — Inskeep IP Group, Inc.

(57) ABSTRACT

Implant engagement mechanisms are disclosed for maintaining engagement with a stent until it has been fully deployed and expanded from a catheter or sheath. The apparatus, method and system involving these engagement mechanisms allow a physician to withdraw or retract a sheath prior to full deployment, thereby allowing for redeployment of the stent at a more desirable position.

20 Claims, 11 Drawing Sheets

Related U.S. Application Data

(60) Provisional application No. 62/220,910, filed on Sep. 18, 2015.

(52) U.S. Cl.
CPC ............... *A61F 2002/9665* (2013.01); *A61F 2230/0069* (2013.01); *A61F 2250/0098* (2013.01)

(58) Field of Classification Search
CPC .... A61F 2/95; A61F 2/962; A61F 2002/9505; A61F 2002/9511; A61F 2002/9522
See application file for complete search history.

(56) References Cited

U.S. PATENT DOCUMENTS

| | | | |
|---|---|---|---|
| 6,776,791 B1 | 8/2004 | Stallings et al. | |
| 6,936,058 B2 | 8/2005 | Forde et al. | |
| 7,309,351 B2 | 12/2007 | Escamilla et al. | |
| 8,241,345 B2 * | 8/2012 | Phung | A61F 2/95 623/1.11 |
| 2001/0049549 A1 | 12/2001 | Boylan et al. | |
| 2002/0016597 A1 | 2/2002 | Dwyer et al. | |
| 2002/0055767 A1 | 5/2002 | Forde et al. | |
| 2002/0120322 A1 | 8/2002 | Thompson et al. | |
| 2002/0120323 A1 | 8/2002 | Thompson et al. | |
| 2004/0267348 A1 | 12/2004 | Gunderson et al. | |
| 2007/0255386 A1 | 11/2007 | Tenne | |
| 2007/0293930 A1 * | 12/2007 | Wang | A61F 2/91 623/1.11 |
| 2008/0300667 A1 | 12/2008 | Hebert et al. | |
| 2011/0264191 A1 | 10/2011 | Rothstein | |
| 2011/0270374 A1 | 11/2011 | Orr et al. | |
| 2012/0078350 A1 * | 3/2012 | Wang | A61F 2/2436 623/2.11 |
| 2012/0239142 A1 | 9/2012 | Lieu et al. | |
| 2013/0123898 A1 | 5/2013 | Tung et al. | |
| 2013/0211492 A1 | 8/2013 | Schneider et al. | |
| 2013/0226278 A1 | 8/2013 | Newell et al. | |
| 2013/0245745 A1 | 9/2013 | Vong et al. | |
| 2013/0245754 A1 | 9/2013 | Blum et al. | |
| 2013/0246745 A1 | 9/2013 | Hatano et al. | |
| 2013/0246754 A1 | 9/2013 | Bradbury et al. | |
| 2014/0107758 A1 | 4/2014 | Glazier | |
| 2014/0200648 A1 | 7/2014 | Newell et al. | |

FOREIGN PATENT DOCUMENTS

| | | |
|---|---|---|
| JP | 2015-513931 A | 5/2015 |
| WO | WO 2004091446 A2 | 10/2004 |
| WO | WO 2011014814 A2 | 2/2011 |
| WO | WO 2013074662 A1 | 5/2013 |
| WO | WO 2013138789 A1 | 9/2013 |

OTHER PUBLICATIONS

European Patent Office, Supplementary Extended European Search Report dated Aug. 2, 2019 in European Patent Application No. 16847564.8, 8 pages.

\* cited by examiner

RELEASABLE DELIVERY SYSTEM

RELATED APPLICATIONS

This application is a continuation of and claims priority to U.S. patent application Ser. No. 15/269,782 filed Sep. 19, 2016 entitled Releasable Delivery System, which claims benefit of U.S. Provisional Application Ser. No. 62/220,910 filed Sep. 18, 2015 entitled Releasable Implant Delivery System, both of which are hereby incorporated herein by reference in their entireties.

BACKGROUND OF THE INVENTION

Medical implants such as stents or stent grafts can also be used to open blood vessels to mitigate the effects of plaque buildup, as a scaffold to keep embolic material within an aneurysm, as a flow diverter to limit blood flow to certain regions, or for other reasons.

Stents or other implants are often delivered with delivery devices comprising a sheath or catheter and an elongated pusher within that catheter. Once the distal end of the sheath is located at a desired location, the sheath is either retracted or the pusher is used to push the stent out of the sheath. However, stents are not always deployed in the precise position that physician may intend, and therefore it can be desirable to retract the stent back into the sheath prior to its final deployment.

SUMMARY OF THE INVENTION

An implant delivery system is described. The implant delivery system can be used for a stent, stent graft, coils, plugs, occluders, or other implants.

One embodiment is directed to a delivery system having a pusher with one or more posts that engage one or more proximal loops of a stent. The posts can be pulled proximally to retrieve the stent back in to its delivery sheath prior to the stent's full deployment.

Another embodiment of the present invention is direct to a delivery system having a pusher with a distal tubular body having a plurality of channels. The channels are positioned around the proximal loops of the stent, allowing the stent to be withdrawn back into its delivery sheath. In one embodiment, the distal end of the tubular body is heat set to radially expand when advanced out of the delivery sheath in an unconstrained position. This expansion causes the width of the channels to increase, releasing the proximal loops of the stent.

In another embodiment, a stent includes a plurality of arm members extending from its proximal end. The arm members have enlarged proximal ends that can engage a plurality of channels on a distal end of a pusher. In one embodiment the channels can be longitudinally offset from each other. In another embodiment, the distal end of the pusher can be heat set to radially expand when not constrained by the delivery sheath, thereby releasing the enlarged proximal ends of the arm members.

In another embodiment, a delivery system includes a pusher with a plurality of wires positioned away from the pusher's core wire. The plurality of wires includes one or more marker bands that are positioned to contact marker coils located on the loops of the stent when the pusher is proximally retracted.

In another embodiment, a stent is disclosed, having a single, triangular loop at its distal end that can be attached to one of the engagement mechanism of the present invention.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1:
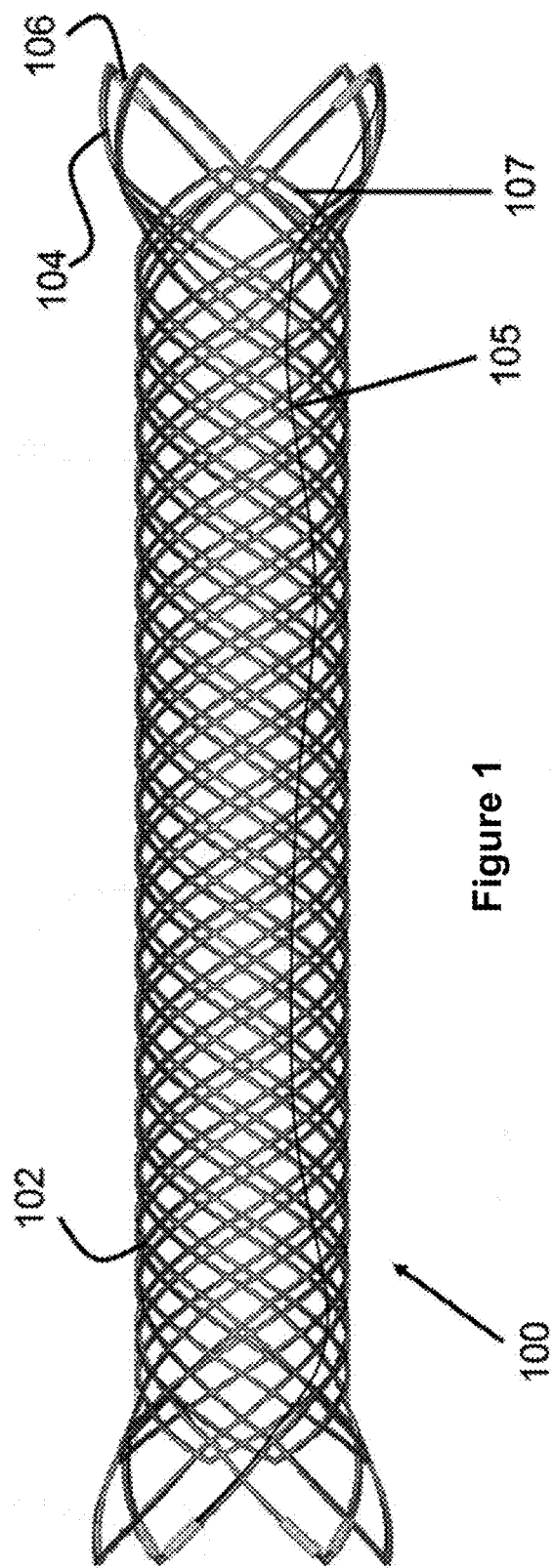
FIGS. 1 and 2 illustrate two embodiments of braided stents that can be used with the engagement mechanisms of the present invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Stents are often delivered with delivery devices comprising a sheath or catheter and an elongated pusher within that catheter. Once the distal end of the sheath is located at a desired location, the sheath is either retracted or the pusher is used to push the stent out of the sheath. However, stents are not always deployed in the precise position that physician may intend, and therefore it can be desirable to retract the stent back into the sheath prior to its full deployment. Embodiments of the present invention are directed to implant delivery devices that engage an implant and allow it to be retracted prior to its final delivery and expansion, thereby allowing for the implant to be repositioned as needed.

Generally, the present specification discusses delivery and engagement mechanisms with regard to stents having proximal loops or similar engagement features. However, it should be understood that other implants are also contemplated for use with these mechanisms, such as stent grafts, microcoils, plugs, occluders, or similar devices.

Figure 2:
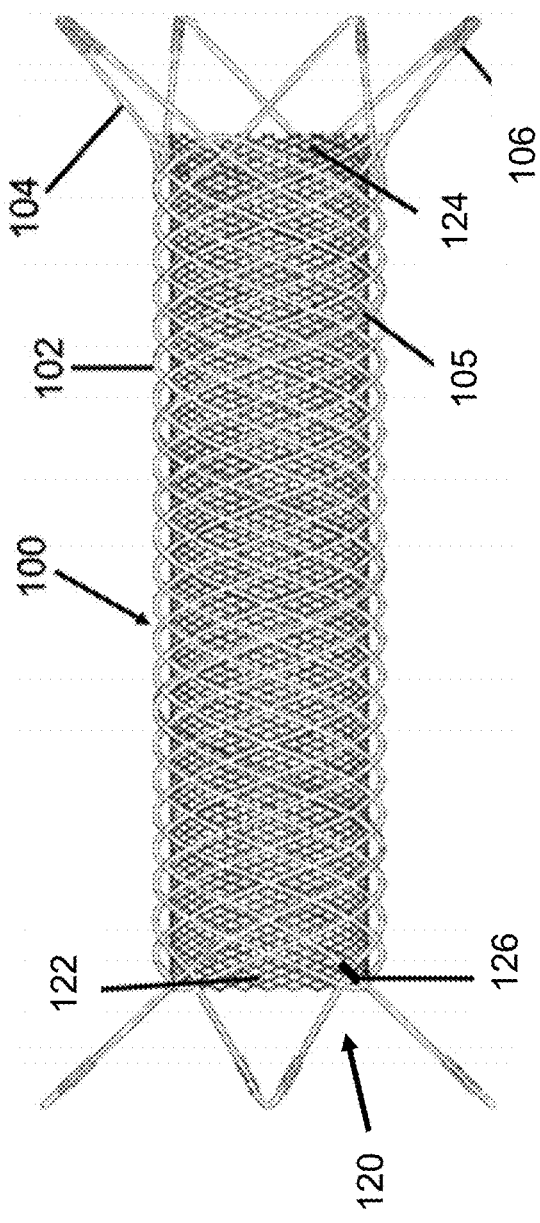

Some embodiments of the present invention engage with stents having loops at their ends and especially their proximal ends. For example, FIG. 1 illustrates a stent 100 woven from one or more wires 102 to have a plurality of larger flared loops 104 and smaller minor loops 107. These flared loops 104 can also have coils 106 and can be connected to a radiopaque wire 105 extending along the length of the stent 100. In another example, FIG. 2 illustrates a dual layer stent 120 having an outer layer 100 similar to FIG. 1 and an inner layer 122 woven from relatively smaller diameter wire 124 than wire 102. These layers 100 and 122 are connected to each other via connector members 126 at either the proximal end or at locations along the length of the stent 120. Additional details of these stents 100 or 120 can be found in U.S. Pub. Nos. 2012/0259404 and 2013/0245745, which are hereby incorporated in their entirety.

Figure 3:
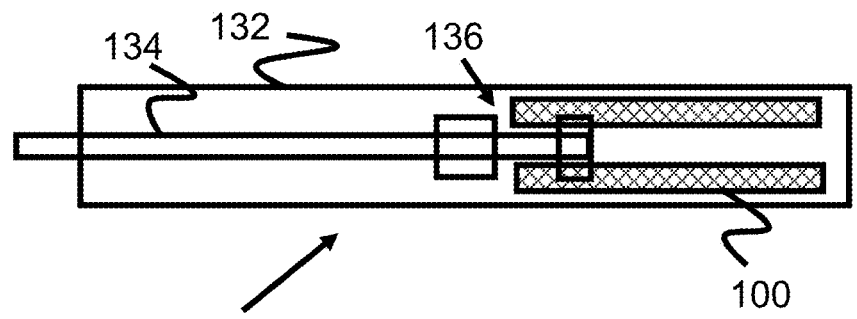
FIGS. 3 and 4 illustrates side cross sectional views of a general engagement system of the present invention.
Figure 4:
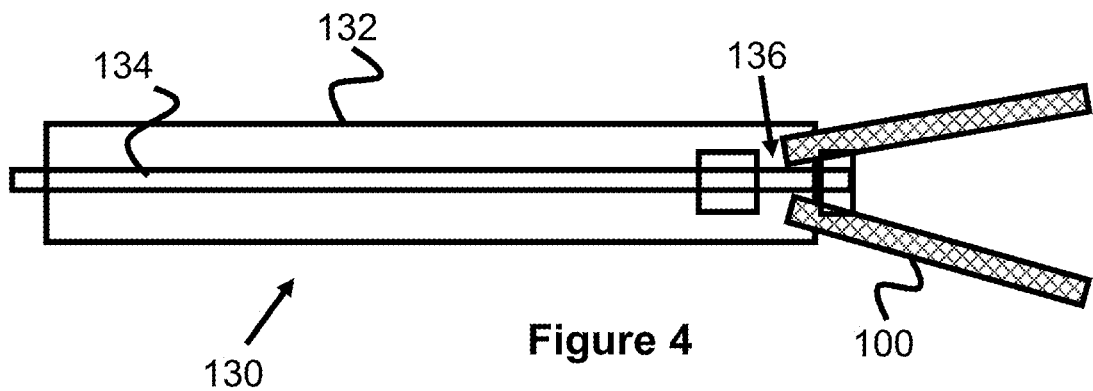

FIGS. 3 and 4 illustrate a basic cross sectional view of a delivery system 130 to demonstrate the basic operation of the stent engagement and retention mechanisms disclosed in this specification. A stent engagement and retention mechanism 136 is located on a distal end of a pusher 134 within a delivery sheath 132. The pusher 134 can be advanced within the sheath 132 (or the sheath 132 can be retracted) to expose the stent 100 and allow it to expand within a patient's vessel. Since the stent engagement mechanism 136 engages the loops 106 of the stent 100 (or other features of the stent 100), the pusher 134 and stent 100 can be retracted prior to the full deployment of the stent 100 (i.e., prior to the stent 100 completely exiting from the sheath 132 and fully radially expanding.

Figure 5:
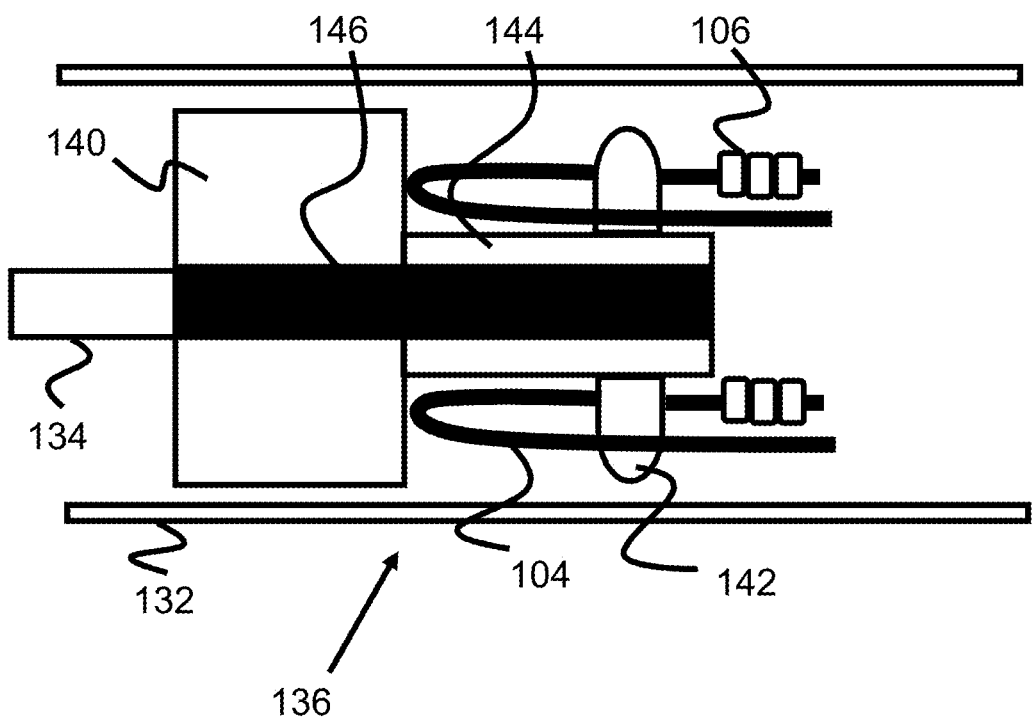
FIGS. 5 and 6 illustrate side views of an embodiment of an engagement system with posts according to the present invention.
Figure 6:
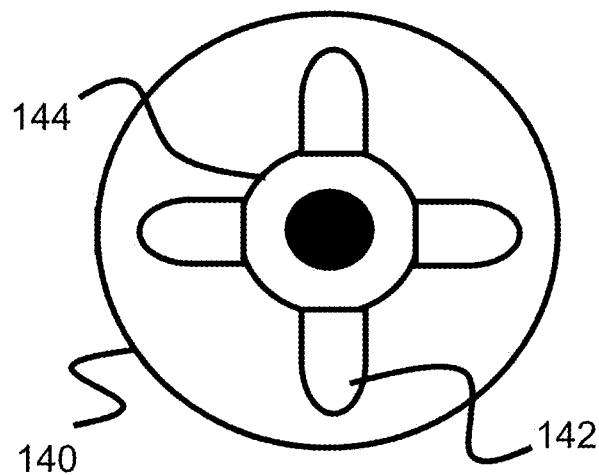

FIGS. 5 and 6 are directed to one example embodiment of a stent engagement mechanism 136, which includes four protruding posts 142 that are positioned through the loops 104 of the stent 100 and can be used to pull the loops 104 distally prior to the full deployment of the stent 100. In this respect, the stent 100 can be retrieved back into the sheath 132 as long as the loops 104 remain positioned around the posts 142.

The posts 142 can extend from radially equidistant locations of the tubular center portion 144 and are spaced distally of the enlarged pushing portion 140. In one example, the posts are generally cylindrical in shape with a rounded top portion. However, the posts 142 can also be rectangular, square, pyramid, or similar shapes. The mechanism 136 may include any number of posts 142, such as 1, 2, 3, 4, 5, 6, 7, and 8. While these posts are disclosed as being located along a single, radial position, the posts 142 can also be offset from each other at alternating distances or can include multiple rows of posts 142 (e.g., 2, 3, or 4 rows). Offset posts can be used, for example, in a system where some posts retain the larger flared loops of the stent and other posts retain the smaller minor loops of the stent.

The posts 142, tubular center portion 144, and the enlarged pushing portion 140 can all be a single unitary member (e.g., all molded as a single piece) or each component can be connected/fixed to each other. The pusher 134 and/or the core wire of the pusher 134 can be fixed within the internal passage 146 of the portions 140 and 144, allowing the pusher 134 to axially move the components within the sheath 132.

In operation, the distal end of the sheath 132 is positioned at or near a desired deployment location within a vessel. The pusher 134 is distally advanced within the sheath 132, causing the enlarged pushing portion 140 to contact a proximal end of the loops 104 and push the stent 100 distally out of the sheath 132. Just prior to the posts 142 exiting the distal end of the sheath 132, the pusher 134 can be proximally withdrawn, causing the posts 142 to contact and pull against the inner proximal portion of the loops 104, thereby pulling the stent 100 back into the sheath 132 for a subsequent deployment attempt.

Figure 7:
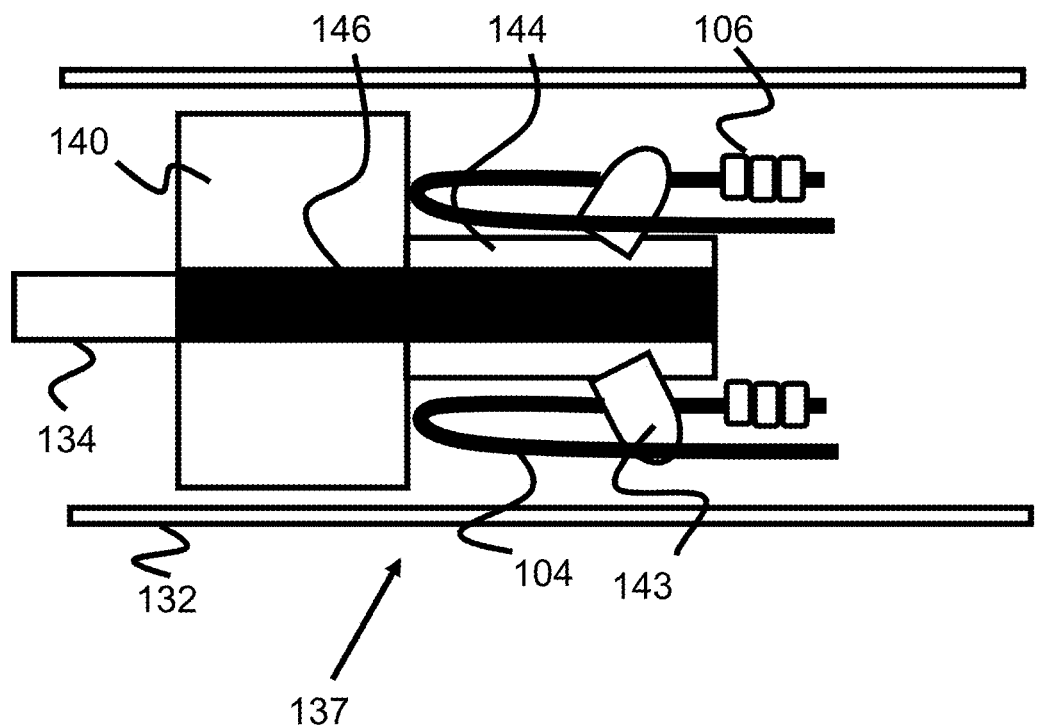
FIG. 7 illustrates a side view of an embodiment of an engagement system with posts according to the present invention.

FIG. 7 illustrates another example embodiment of a stent engagement mechanism 137 that is generally similar to the previously described mechanism 136, but includes distally-angled posts 143 (i.e., distally angled ends of the posts 143) that may allow for the loops 104 of the stent 100 to more easily slide off and disengage with the mechanism 137 during final deployment. In one example, the posts 143 can be angled between about 90 and about 45 degrees relative to the surface of the tubular center portion 144. In an alternate example embodiment, one or more of the posts 143 can be angled at different angles (e.g., some posts angled at 45 degrees and others angled at 60 degrees). In another alternate example embodiment, the posts 143 can be proximally-angled at angles similar to those described above to better retain the loops 104 of the stent 100 during retraction.

Figure 8:
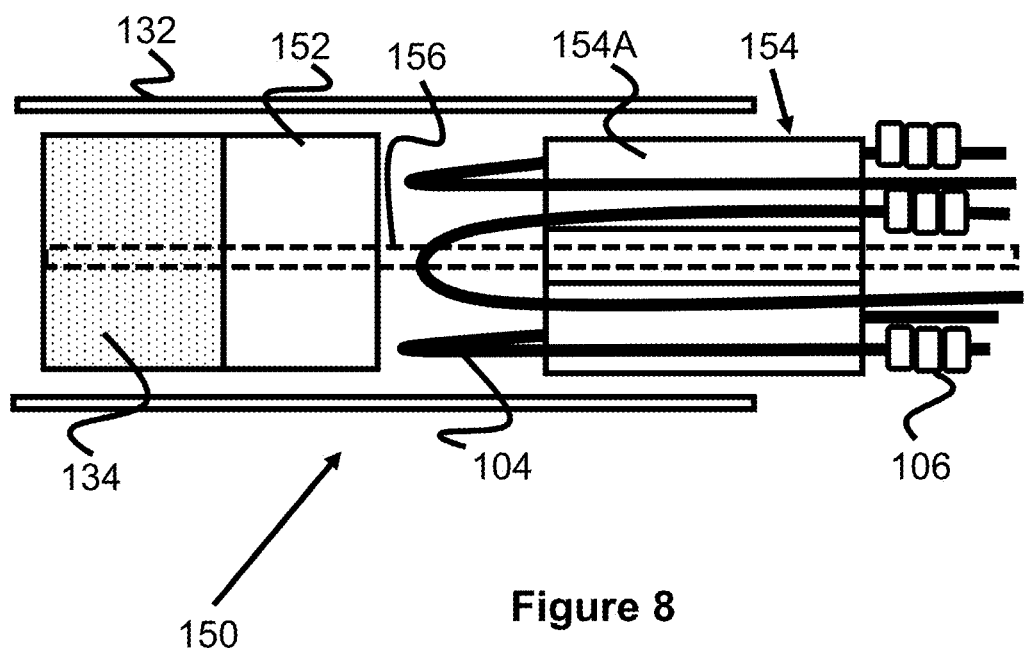
FIGS. 8 and 9 illustrate side views of an embodiment of an engagement system with elongated block members according to the present invention.
Figure 9:
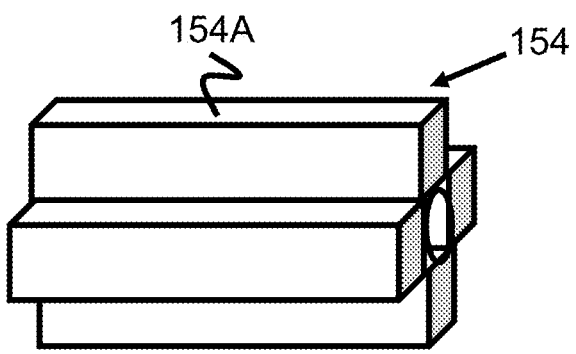
Figure 10:
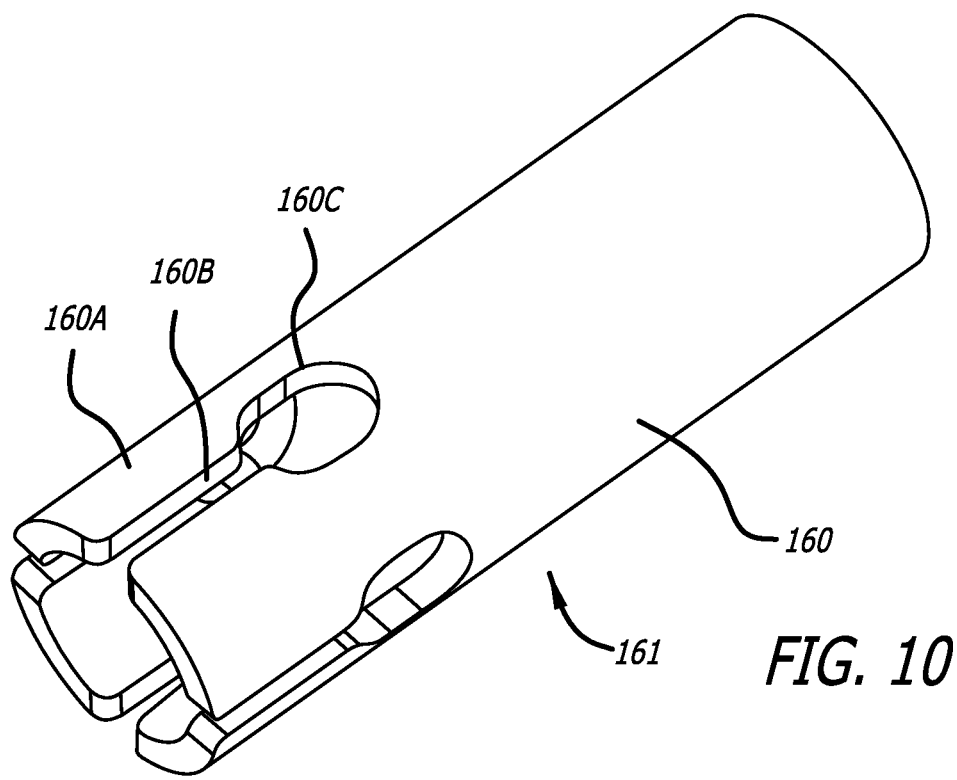
FIGS. 10-15 illustrate various views of an embodiment of an engagement system with channels according to the present invention.
Figure 11:
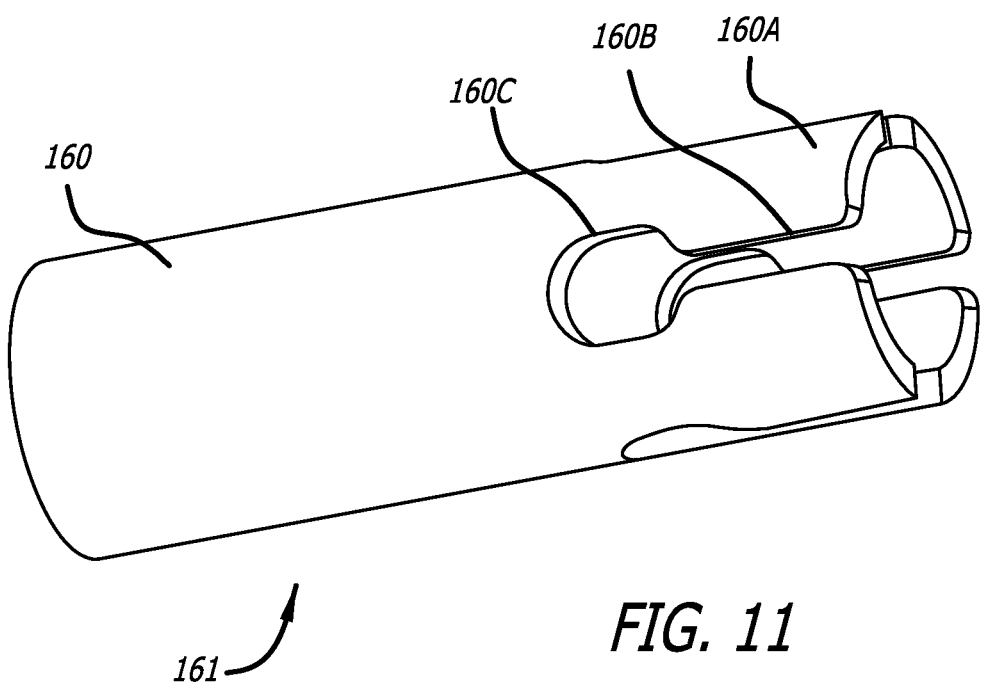

FIGS. 8 and 9 illustrate another example embodiment of a stent engagement mechanism 150 that includes a retention block 154 having a plurality of axially elongated rectangular shapes 154A that are sized to engage the loops 104 of the stent 100. For example, the retention block 154 of FIG. 9 includes four rectangular shapes 154A, but 1-20 shapes 154A (or more) are also possible. The retention block 154 is preferably fixed distally and away from a cylindrical pusher block 152, both being connected to a core wire 156 of the pusher. The pusher block 152 is also preferably composed of radiopaque material so as to act as a visually distinctive marker band. In operation, the retention block 154 and the pusher block 152 function similar to the prior described embodiments, pulling and pushing the loops 104 of the stent 100, respectively, through the sheath 132.

The rectangular shapes 154A are illustrated with abrupt proximal and distal ends having edges. However, the ends of these shapes 154A (particularly the distal end that contacts the loops 104) can alternately have a rounded or blunted shape.

FIGS. 10-15 are directed to yet another stent engagement mechanism 161 that can be fixed to a pusher 134 and used to retrieve a stent 100 back into a sheath 132 prior to full deployment. Specifically, the stent retention mechanism 161 includes a tubular body 160 that is fixed to the end of the pusher 134 and can engage and disengage the loops 104 of the stent 100 by closing when inside the sheath 132 and opening when outside the sheath 132. The distal end of the tubular body 160 includes a plurality of elongated channels 160B that extend proximally and then widen to enlarged channel portions 160C. These channels 160B and 160C effectively create axially elongated distal finger portions 160A from the tubular body portion 160. In one example, the tubular body 160 includes four symmetrical, radially equidistant channels 160B, 160C that correspond to the positions of at least some of the loops 104 of the stent 100. However, additional channels can be created to correspond to the loops 104 of the stent 100 (e.g., 6 or 8).

Figure 14:
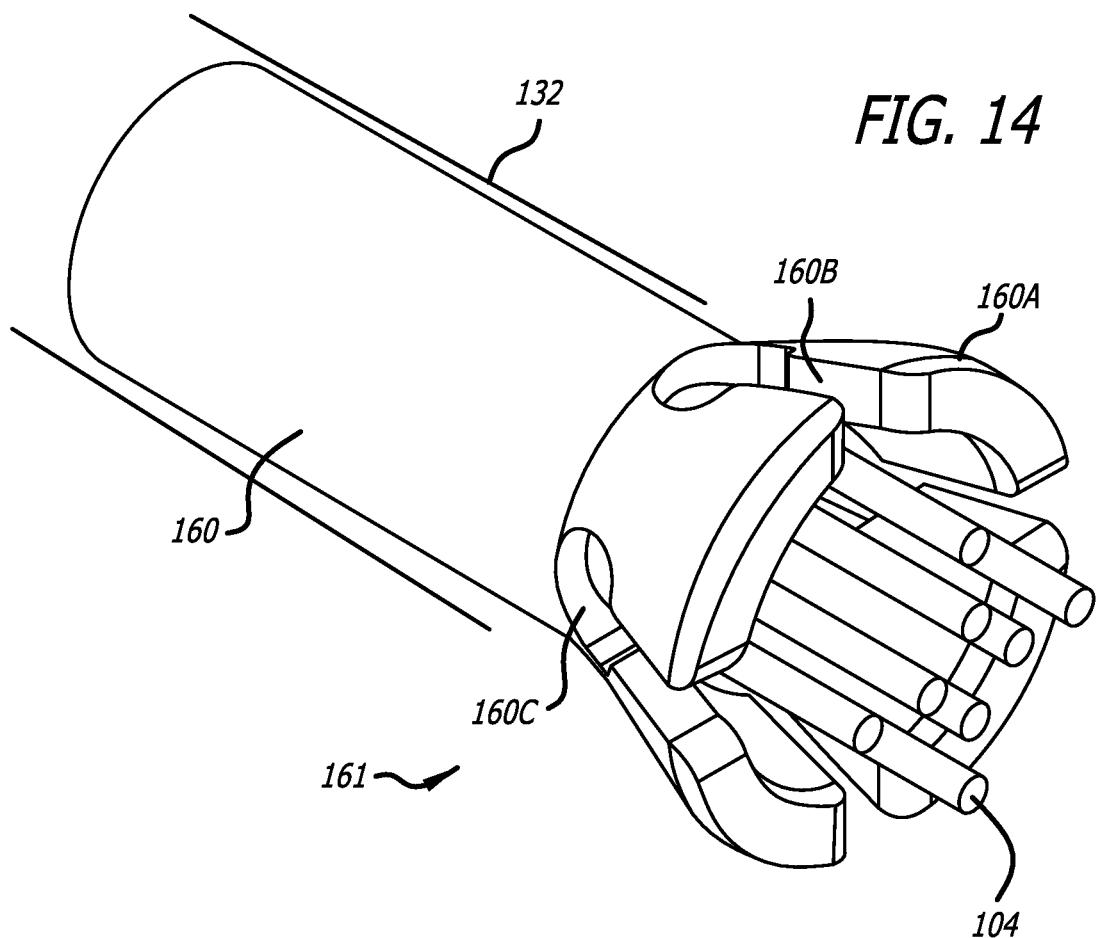
Figure 15:
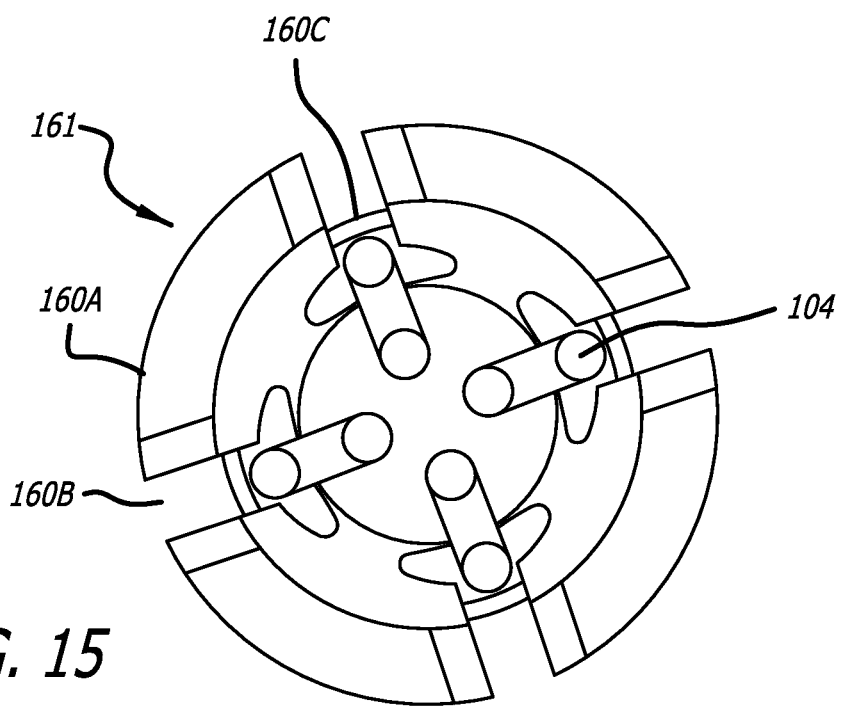

In one embodiment, the finger portions 160A are heat set to radially expand when unrestrained, as seen in FIGS. 14 and 15. In other embodiments, the finger portions are jointed or bendable so that the radially expandable force of the stent 100 expands against the fingers 160A and radially expands them. It should be noted that the further proximal the enlarged channel portions 160C are located, the potentially slower the expansion and deployment of the stent 100 may occur as it is pushed distally outwards. Additionally, further proximal positioning may increase the retention strength of the mechanism 161.

Figure 12:
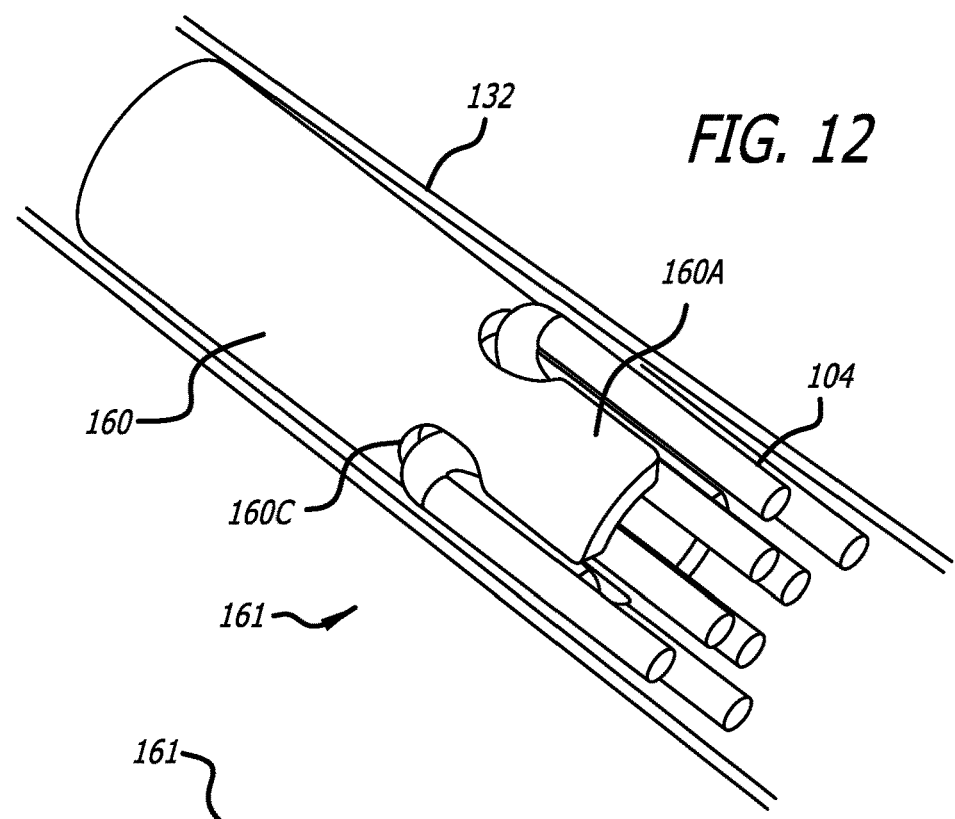
Figure 13:
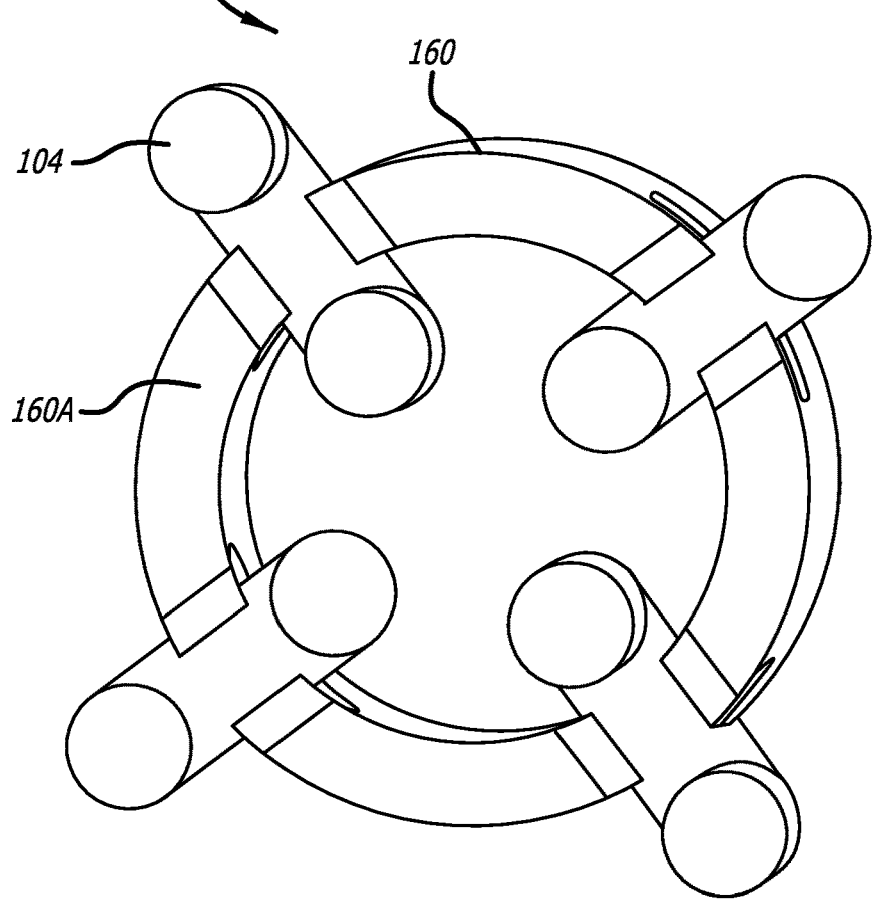

In its compressed configuration, the proximal end or bend of the loops 104 of the stent 100 are located in the enlarged channel portion 160C, and the relatively straight, adjacent portions of the loops 104 distally extend above and below the channel portion 160B. Since the enlarged channel portion 160C has a width large enough to accommodate the proximal end portion of the loops 104 of the stent 100, but the narrower elongated channel portions 160B are too narrow for the width of the loop 104 when in its compress configuration, the loops 104 and therefore the stent 100 remain engaged with the tubular body 160 when compressed within the sheath 132, as seen in FIGS. 12 and 13.

Mechanism 161 can be manufactured in a variety of ways in order to create the radially expandable finger portions. In one embodiment, a material with a similar diameter to the diameter of the mechanism is placed within the mechanism. Materials of progressively larger diameter are subsequently introduced within the mechanism and the mechanism is heat set over time. In this way, the shape memory is built into the finger portions of the mechanism so that the finger portions expand when not restrained by a sheath or catheter.

As the pusher 134 is distally advance through the sheath 132 and the stent 100 is pushed out of the distal end of the sheath 132, the finger portions 160A of the tubular body 160 remain in their radially compressed configuration, thereby retaining the stent 100. However, when the distal end of the tubular body 160 and therefore the finger portions 160A are extended out of the distal end of the sheath 132, the finger portions 160A radially expand, thereby increasing the width of the elongated channels 160B, as seen in FIGS. 14 and 15, allowing the loops 104 to distally pass through the channels 160B and be released. Thus, until the finger portions 160A pass beyond the distal end of the sheath 132, the stent 100 can be retrieved and withdrawn back into the sheath 132 for later deployment.

U.S. Pub. Nos. 2010/0268204 and 2015/0289879 detail thermal detachment systems which can also be used with the previously described engagement mechanism 161 (or any of the other embodiments of this specification) and are hereby incorporated by reference in their entirety. In one embodiment, filaments (polymer or metallic) or sutures may be wound between the channels 160C of the tubular body 160 and released similar to the stent loops 104.

Alternatively, a portion of the stent 100 may be placed over channels 160C and filaments or sutures may be used to hold the stent 100 over the channels. The tension imparted by the filaments and/or sutures would keep tubular body 160 in a closed configuration until broken, upon which the section would expand to its pre-set expanded shape. A detachment system, such as a mechanical system or the thermal detachment system incorporated above, may be used to break the filaments/sutures or the retention mechanism for the mesh to remove the retaining force and allow the fingers 160A to expand. This configuration may be desirable in a situation where the user may desire more control over deployment.

Figure 16:
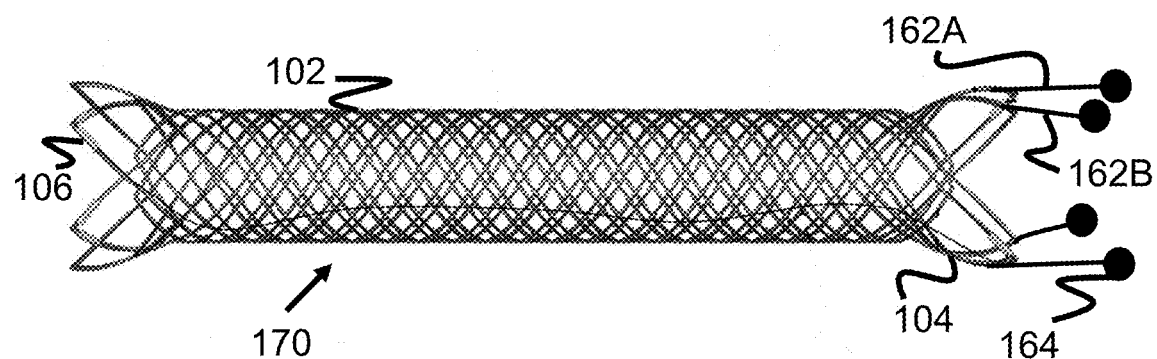
FIG. 16 illustrates a side view of an embodiment of a stent having elongated proximal arms according to the present invention.

While the previously described stent engagement mechanisms may releasably interlock with the loops 104 of the stent 100, other engagement mechanisms may interlock with retention arms on the proximal end of the stent 100. For example, FIG. 16 illustrates a stent 170 having elongated arms 162A/162B fixed to the loops 104, extending proximately, and terminating with an enlarged region or rounded portion 164. These proximally extending arms 162A/162B and rounded portions 164 allow an engagement mechanism to engage a proximal region that is spaced apart from the main body of the stent 170, thereby allowing the stent 170 to almost fully expand without its release from the pusher 134.

Figure 17:
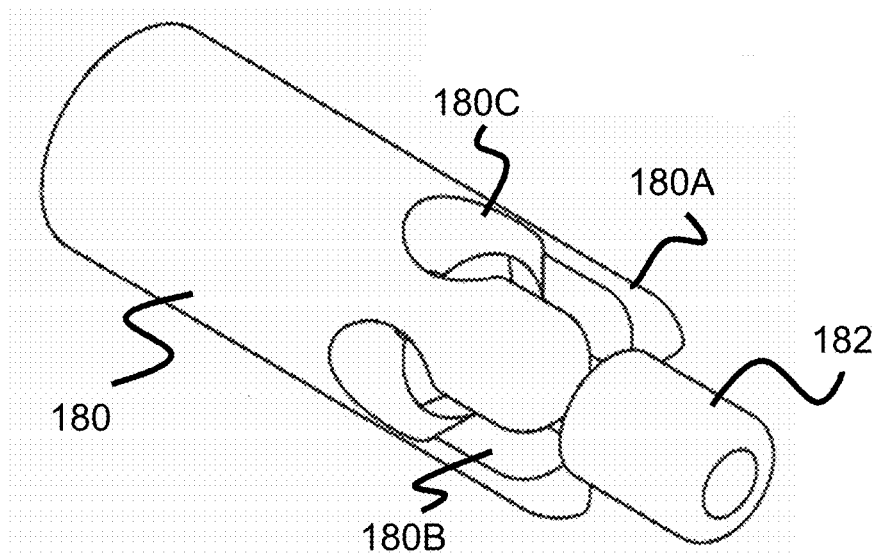
FIG. 17 illustrates a view of an embodiment of an engagement system with channels that engages the stent of FIG. 16, according to the present invention.

FIG. 17 illustrates one such stent engagement mechanism comprising a tubular body 180 that can be fixed to a distal end of the pusher 134. Similar to previous embodiments, the tubular body 180 includes a distal end with a plurality of channels. The channels preferably include a narrower width distal portion 180B and a relatively wider proximal portion 180C that terminates the channels. The wider proximal portion of the channel 180C is sized to allow the rounded portion 164 to pass into it, while the narrower width channel portion 180B may accommodate at least some of the arms 162A/162B, while contained in the sheath 132. The finger portions 180A formed by the channels are preferably connected to a cylindrical support and radiopaque marker member 182 through which a core wire of the pusher 132 or a guidewire can be located.

Similar to previous embodiments, as long as the finger portions 180A and wider channel portions 180C remain in the sheath 132, the stent 170 can still be withdrawn back into the sheath 132 after being mostly deployed within a vessel. However, once the pusher 134 advances out the distal end of the sheath 132, the arms 162A and 162B radially expand outwards, pulling the rounded portions 164 out of the wider proximal portions 180C of the tubular body 180 to fully release the stent 100.

Figure 18:
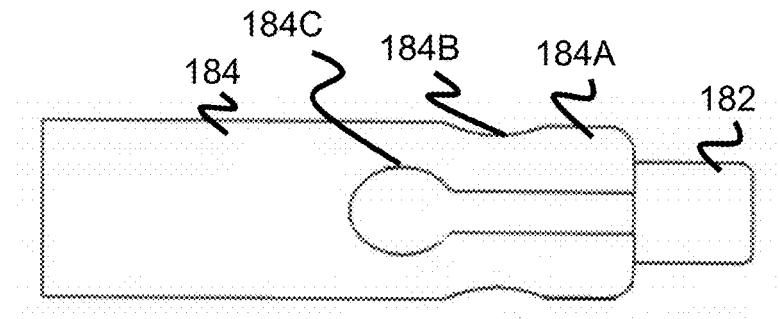
FIGS. 18 and 19 illustrate views of an embodiment of an engagement system with channels that engages the stent of FIG. 16, according to the present invention.
Figure 19:
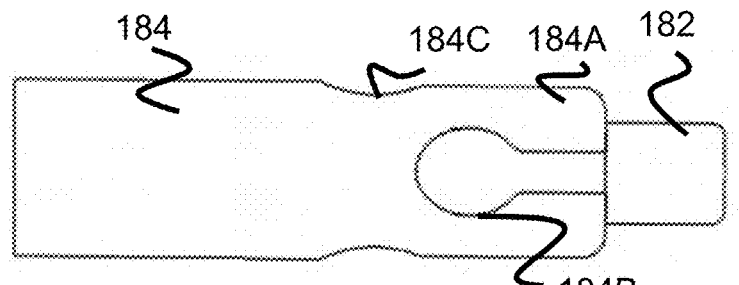

FIGS. 18 and 19 illustrate a tubular member 184 that is generally similar in function and operation to the previously described tubular member 180. However, the tubular member 184 includes some wider channel portions 184B that are closer to the distal end of the tubular member 184 and some wider channel portions 184C that are located proximally of the channel portions 184B. In that regard, the stent 170 can include relatively longer arms 162A extending from some loops 104 to fit into and engage with the proximal channel portion 184C and relatively shorter arms 162B extending from other loops 104 to fit into and engage with distal channel portion 184B. By offsetting the channel portions 184B and 184C, additional radial space can be otherwise gained, allowing for a greater number channels to be potentially used.

In one example, the length of the arms 162A/162B can alternate circumferentially between the shorter arms 162B and the longer arms 162A, while the distal and proximal channel portions 184B/184C can similarly alternate. In one embodiment, the distal channel portions 184B are located on opposite sides of the tubular member 184 from each other and the proximal channel portions 184C are similarly located on opposite sides of the tubular member 184 from each other, all of which being radially separated from each other by an equidistant degree amount. As in previous embodiments, the finger portions 184A are connected to a distal support cylinder 182 that allows passage of a core wire of the pusher member 134 and further may act as a radiopaque marker.

Figure 20:
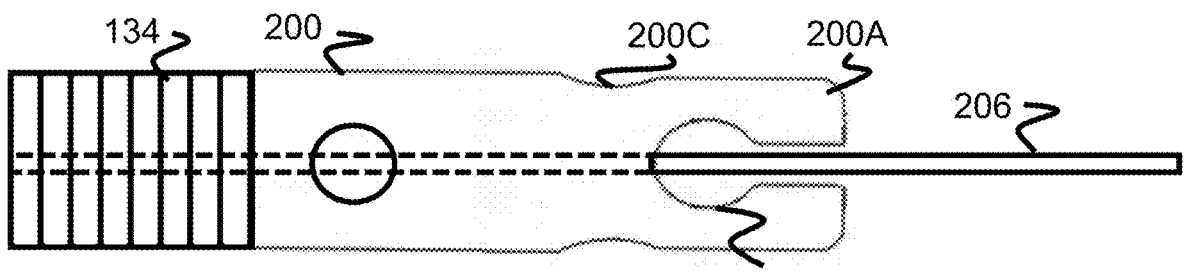
FIGS. 20 and 21 illustrate views of an embodiment of an engagement system with channels that engages the stent of FIG. 16, according to the present invention.
Figure 21:
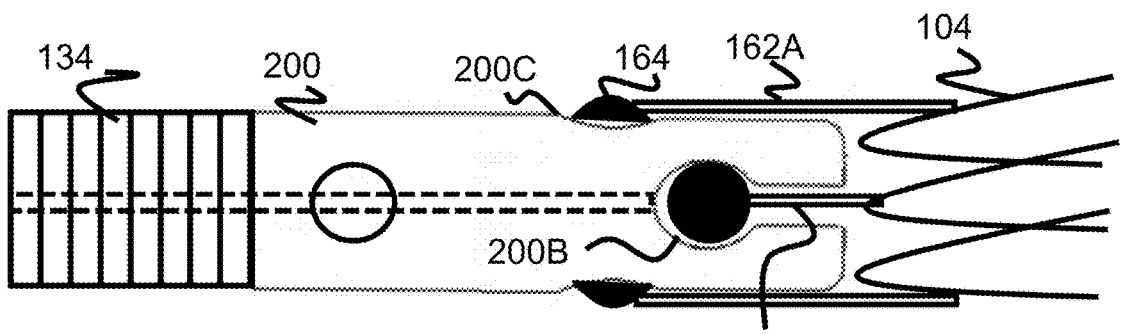

FIGS. 20 and 21 illustrate another embodiment of a tubular member 200 that is similar to the previously described tubular member 184, having wider proximal channel portions 200C and wider distal channel portions 200B. However, no distal support cylinder 182 is present, allowing the distal ends of the finger portions 200A to be free.

In one embodiment, the finger portions 200A remain in their radial positions as they exit the distal end of the sheath 132, maintaining the size of the distal and proximal channels 200B, 200C. In another embodiment, the finger portions 200A are heat set to radially expand, and therefore remain radially compressed when located in the sheath 132 and radially open or "flower" when moved outside of the sheath 132. Once radially open, the distal and proximal channels 200B, 200C also increase in size, allowing the rounded portions 164 to more easily release.

As in the prior embodiments having a tubular member, the core wire 206 of the sheath 134 is positioned through the tubular member 200 and further distally to the distal end of the stent 100. This positioning allows the stent 100 to be compressed over the core wire 206 and may provide additional friction to help pull the stent 100 out of the sheath 134.

Figure 22:
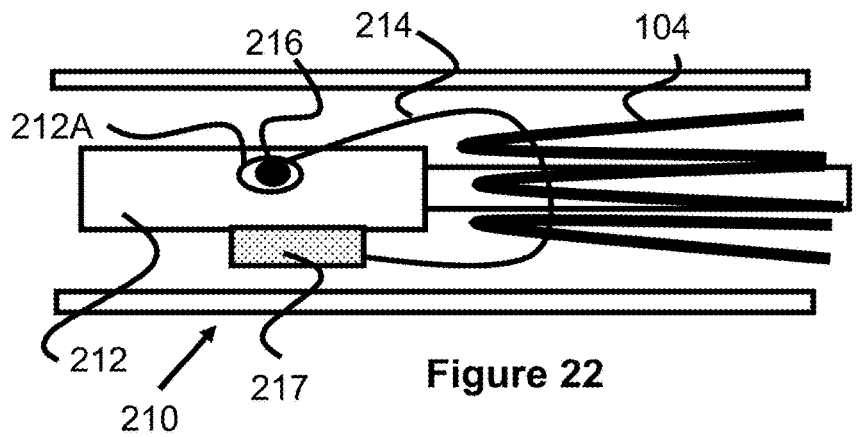
FIG. 22 illustrates a view of an embodiment of an engagement system with a retention wire according to the present invention.

FIG. 22 illustrates another embodiment of a stent engagement mechanism 210 in which a retention wire 214 passes through at least some of the loops 104 of the stent 100 and is releasably connected to a distal portion 212 of the pusher 234. One end of the retention wire 214 is welded or bonded along location 217 to the distal portion 212 of the pusher 234. The opposite end of the retention wire 214 includes an enlarged rounded portion 216 that fits within an aperture or notch 212A on the distal portion 212.

While in the sheath 132, the rounded portion 216 remains in the notch 212A, maintaining the retention wire 214 in a closed loop though the stent loops 104. In this respect, the stent 100 can be completely or nearly completely deployed out of the sheath 132 and then retracted back into the sheath 132 for later redeployment. Once the desired location of the stent 100 is achieved, the pusher 134 can be further distally advanced so that the distal portion 212 and notch 213A are exposed outside of the sheath 132. This position allows the rounded portion 216 to move out of the notch 212A, opening the loop created by the retention wire 214. The pusher 134 can be proximally withdrawn, pulling the retention wire 214 back into the sheath 132.

While only one retention wire 214 and notch 216 are illustrated in FIG. 22, a plurality can also be included (e.g., 2-6). These plurality of retention wires 214 may pass through different loops 104 or all of the same loops 104. The retention wires 214 can be composed of a metal, such as Nitinol, and can be heat set to straighten or can be of a stiffness to resist bending and generally straighten when unconstrained.

Figure 23:
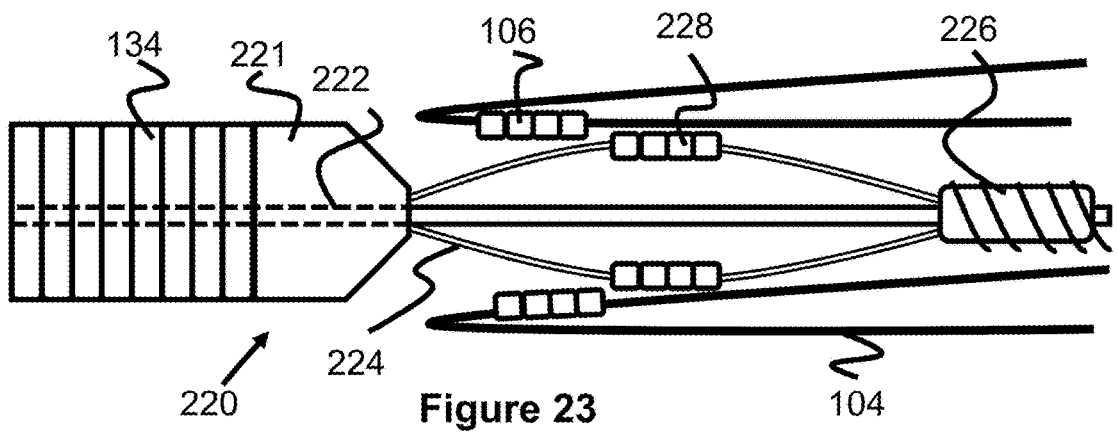
FIG. 23 illustrates a view of an embodiment of an engagement system with radially offset marker bands according to the present invention.

FIG. 23 illustrates yet another embodiment of a stent engagement mechanism 220 having a plurality of pusher marker bands 228 that can be used to contact and pull against the marker coils 106 on the stent loops 104, thereby pulling the stent 100 back into the sheath 132. The pusher marker bands 228 can be fixed on a wire 224 that is connected at a proximal marker band 221 and a distal bonding location 226 (e.g., a marker band or weld), and is bent or bowed away from the core wire 222 of the pusher 134. Since the marker bands 228 "float" relative to the core wire 222 (or alternately a guidewire), relatively more freedom of movement of the marker bands 228 may be provided (as opposed to a static fixture directly bonded to the core wire 222) and may thereby provide better engagement with the marker coils 106 of the stent loops 104.

Two wires 224 are illustrated in FIG. 23, but any number of wires 224 corresponding to marker coils 106 can be used (e.g., 1-8). Each wire 224 can include any number of marker bands 228, such as 1-4 bands. The proximal marker band 221 may be formed from a tube, wound coil, or similar structures and, as the pusher 134 is distally advanced, pushes on the proximal ends of the loops 104 to advance the stent 100 out of the sheath 132.

As with previous embodiments, the stent 100 can be almost fully deployed out of the sheath 132 and retracted back into the sheath 132. Specifically, if the proximal end of the stent 100 remains compressed such that the marker coils 106 can still be contacted by the marker bands 228, retracting the pusher 134 will cause the proximal end of the marker bands 228 to contact the distal ends of the marker coils 106, thereby pulling the stent 100 proximally within the sheath 138 for later redeployment.

Figure 24:
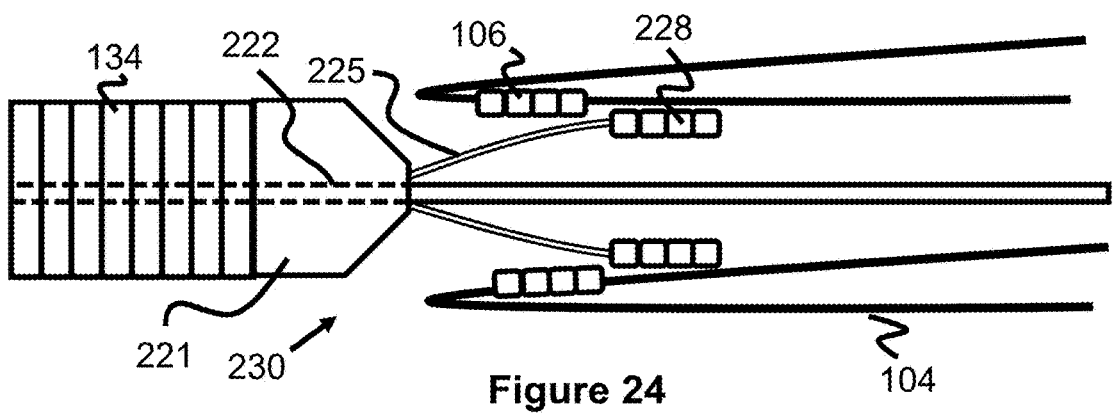
FIG. 24 illustrates a view of an embodiment of an engagement system with radially offset marker bands according to the present invention.

FIG. 24 illustrates a stent engagement mechanism 230 that is nearly identical to the previously described mechanism 220. However, instead of using bowed wires 224 that are connected at proximal and distal locations, the wires 225 are connected only at the proximal marker band 221 and extend radially outwards. The marker bands 228 are located at or near the distal end of the wire 225 and are thereby radially spaced apart from the core wire 222. In this respect, the marker bands 228 are positioned in a similar location as the embodiment of FIG. 23 to allow for contact with the marker coils 106 of the stent 100 when the pusher 134 is proximally retracted. Again, only two wires 225 are illustrated in FIG. 24, but a plurality of wires are possible (e.g., between 2-8 wires).

Figure 25:
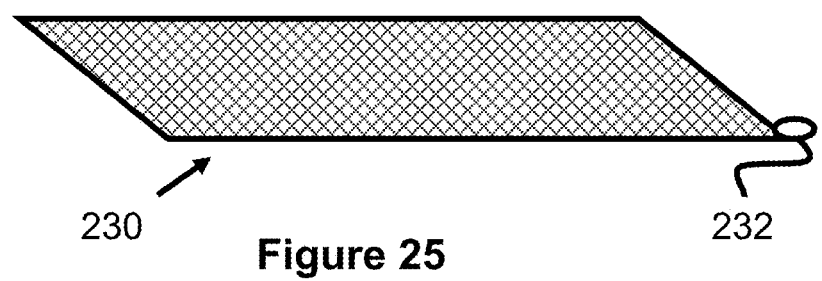
FIGS. 25 and 26 illustrate views of a stent having a single proximal loop for connecting with an engagement system according to the present invention.
Figure 26:
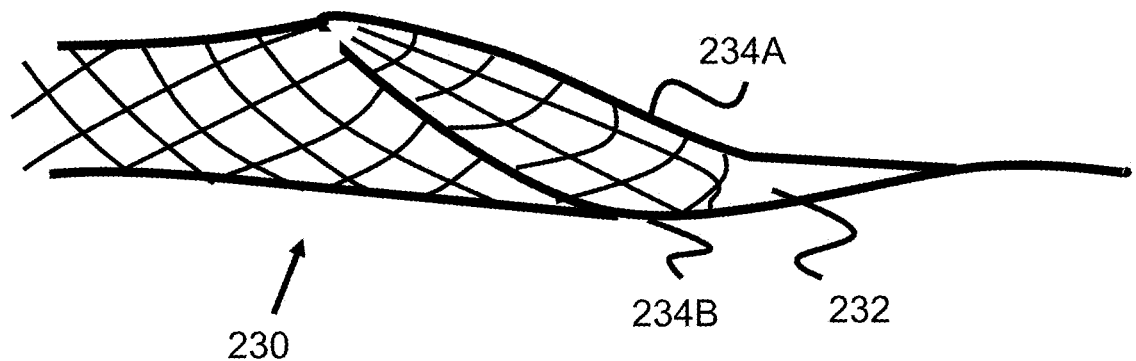

FIGS. 25 and 26 illustrates a braided stent 230 that is woven to have a relatively larger, single, proximal loop 232, which allows the stent 230 to be fully deployed from the sheath 132 and then retracted back into the sheath 132. Preferably, the end wires of stent 230 are welded to two symmetrically curved wires 234A and 234*b* to form an angled proximal end that terminates proximally in a "V" shaped loop 232. The two wires 234A and 234B are preferably welded to each other only at proximal most end of the stent 230, and not near their opposite ends at the stent's top, which allows the loop formed by the wires 234A, 234B to more easily collapse within the sheath 134. This proximal loop stent 230 provides a spaced-apart proximal loop 232 that can be connected to many of the stent engagement mechanisms previously discussed in this specification, such as mechanism 210.

The two wires 234A and 234B can have a larger diameter than the other wires that make up the stent 230, thereby increases the ease of welding these wires together. The two wires 234A and 234B can be separate and discrete from those braided in the stent body, or can be braided with the other wires along the length of the stent 230. Preferably, the other wires making up the body of the stent are welded to the underside of the wires 234A and 2346.

Generally, unless otherwise noted, the components of the previously described embodiments can have components comprised of a shape memory allow, such as Nitinol, and/or polymers.

Implant delivery system materials were described earlier. In some embodiments the implant delivery system is comprised of multiple tubes or multiple elements which are affixed together. In these embodiments, the material for some sections of the delivery system may be different than the material in other sections. Thus, for example, a more proximal section of the implant delivery system could utilize a high strength material to promote high push strength while a more distal section of the implant delivery system could utilize material with a high shape memory to augment the radially expansile "flowering" effect shown in FIG. 14.

The previously described delivery system embodiments can have a variety of diameters to accommodate various stent sizes and catheter sizes. In one example, the delivery system can have a diameter of about 0.005" to about 0.05".

The implant delivery systems of the present specification can be used to deliver a variety of implants, such as various occluders, embolic coils, or other implants, though the term "stent" is used throughout this specification for convenience.

Please note while the term catheter or sheath is used occasionally within the specification to discuss a structure through which the implant delivery system is used, the delivery system can be used in a variety of delivery devices such as hypotubes or other delivery devices. Thus the implant delivery system can be used to deliver an implant through any type of delivery device.

Please note figures shown are meant only as representations and/or illustrations to aid in understanding, and not limited to what is explicitly shown. Similarly, any measurements are meant only as illustrative examples to aid in understanding and are not meant to be limiting.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A vessel prosthesis delivery device comprising:
a pusher configured to deliver the vessel prosthesis through a sheath;
a distal end of the pusher having a plurality of elongated channels spaced circumferentially around the pusher; the distal end having 1) a radially compressed configuration and 2) a radially expanded configuration in which the plurality of elongated channels have a larger width than in the radially compressed configuration;
wherein the plurality of elongated channels are configured to engage a proximal portion of the vessel prosthesis in the radially compressed configuration and release the proximal portion of the vessel prosthesis when the elongated channels have the larger width than in the radially compressed configuration.

2. The vessel prosthesis delivery device of claim 1, wherein the plurality of elongated channels of the pusher are configured to accommodate a plurality of arms and a plurality of enlargements on the vessel prosthesis.

3. The vessel prosthesis delivery device of claim 1, wherein the plurality of elongated channels are further configured to accommodate a plurality of arms and a plurality of enlargements which are connected to proximal end loops of the vessel prosthesis.

4. The vessel prosthesis delivery device of claim 1, wherein each of the plurality of elongated channels include a narrow channel section and a wide channel section.

5. The vessel prosthesis delivery device of claim 4, wherein the wide channel section is at a proximal end of the elongated channel.

6. The vessel prosthesis delivery device of claim 5, wherein the wide channel sections are in different longitudinal areas of the pusher, such that some wide channel sections are distal relative to other wide channel sections.

7. The vessel prosthesis delivery device of claim 1, wherein the pusher is tubular and has a length that spans at least to a proximal end of the sheath.

8. The vessel prosthesis delivery device of claim 7, wherein the pusher accommodates a core wire that spans a distal section of the elongated pusher.

9. The vessel prosthesis delivery device of claim 8, further comprising a cylindrical member adjacent the distal end of the pusher, where the cylindrical member accommodates the core wire.

10. The vessel prosthesis delivery device of claim 9, wherein the cylindrical member is radiopaque.

11. The vessel prosthesis delivery device of claim 1 wherein the distal end of the pusher radially expands when not constrained within the sheath.

12. The vessel prosthesis delivery device of claim 1, wherein the plurality of elongated channels of the pusher accommodate a plurality of proximal end loops of the vessel prosthesis.

13. A vessel prosthesis delivery system comprising:
a sheath;
a pusher;
a distal end of the pusher comprising a tubular member having a plurality of circumferentially spaced elongated channels; the tubular member having a radially compressed configuration and a radially expanded configuration;
wherein the plurality of elongated channels engages a proximal portion of the vessel prosthesis in the radially compressed configuration in order to deliver the vessel prosthesis through the sheath and wherein the plurality of elongated channels increase in width in the radially expanded configuration relative to the radially compressed configuration to disengage the vessel prosthesis from the distal end of the pusher.

14. The vessel prosthesis delivery device of claim 13 wherein the distal end of the pusher radially expands when not constrained within the sheath.

15. The vessel prosthesis delivery device of claim 14, wherein the distal end of the pusher is heat set to radially expand when not constrained within the sheath due to shape memory.

16. The vessel prosthesis delivery device of claim 14, where a section of the pusher which radially expands when not constrained within the sheath includes the plurality of elongated channels.

17. The vessel prosthesis delivery device of claim 13, wherein each of the plurality of elongated channels include a narrow channel section and a wide channel section.

18. The vessel prosthesis delivery device of claim 17, wherein the narrow channel section accommodates an arm element extending from a proximal end loop of the vessel prosthesis and the wide channel section accommodates an enlargement connected to the arm element.

19. The vessel prosthesis delivery device of claim 13, wherein the plurality of elongated channels of the pusher accommodate a plurality of proximal end loops of the vessel prosthesis, such that a portion of the loops sit above the elongated channels and a portion of the loops sit under the elongated channels.

20. A method of delivering a vessel prosthesis comprising:
- pushing an elongated pusher releasably connected to the vessel prosthesis through a sheath;
- a distal end of the elongated pusher having a plurality of elongated channels spaced circumferentially around the tubular member, wherein the plurality of elongated channels engages a proximal portion of the vessel prosthesis;
- the vessel prosthesis having a first collapsed configuration when within the sheath and a second expanded configuration when not within the sheath; and,
- radially expanding the distal end of the elongated pusher to increase the widths of the plurality of elongated channels to disengage the proximal portion of the vessel prosthesis.

* * * * *